United States Patent [19]

Mawhinney

[11] Patent Number: 4,638,808
[45] Date of Patent: Jan. 27, 1987

[54] CIRCUIT FOR SEPARATING ONE TYPE SIGNAL COMPONENT FROM ANOTHER

[75] Inventor: Daniel D. Mawhinney, Livingston, N.J.

[73] Assignee: RCA Corporation, Princeton, N.J.

[21] Appl. No.: 641,464

[22] Filed: Aug. 16, 1984

[51] Int. Cl.$^4$ .............................................. A61B 5/04
[52] U.S. Cl. .................................................... 128/653
[58] Field of Search ............................... 128/695–696, 128/698, 653, 721; 307/517, 518, 522

[56] References Cited

U.S. PATENT DOCUMENTS

| | | |
|---|---|---|
| 2,820,361 | 1/1958 | Apps . |
| 3,689,879 | 9/1972 | Brudick . |
| 3,879,576 | 4/1975 | Okada et al. . |
| 4,182,315 | 1/1980 | Vas . |
| 4,270,545 | 6/1981 | Rodler . |
| 4,289,981 | 9/1981 | Sakamoto et al. . |
| 4,357,944 | 11/1982 | Mauser . |

*Primary Examiner*—Henry J. Recla
*Assistant Examiner*—Francis J. Jaworski
*Attorney, Agent, or Firm*—Joseph S. Tripoli; Robert L. Troike; Raymond E. Smiley

[57] ABSTRACT

A signal component separating circuit is responsive to a signal having a pulsing component and a reciprocating component for providing a signal corresponding to the pulsing component. The circuit includes first and second channels the outputs of which are coupled to respective inputs of a comparator circuit which produces the signal corresponding to the pulsing component of the input signal.

Each of the channels includes a peak detection and holding circuit which includes a charging and discharging circuit. The second channel peak detection and holding circuit has a faster charging and discharging time than the first channel peak detection and holding circuit. The second channel peak detection and holding circuit attenuates the input signal more than the first channel peak detection and holding circuit. As a result the signal in the first channel is greater in amplitude than the signal in the second channel except when the pulses are present.

11 Claims, 2 Drawing Figures

CIRCUIT FOR SEPARATING ONE TYPE SIGNAL COMPONENT FROM ANOTHER

The Government has rights in this invention pursuant to Contract No. DAMD17-83-C-3018, awarded by the Department of the Army.

BACKGROUND OF INVENTION

1. Field of Invention

The present invention is directed to a circuit for separating one type signal component, such as pulses, from another type signal component, such as a slowly reciprocating component, and more particularly to such a circuit for separating components where the respective frequencies of the signal components are about the same.

2. Description of the Prior Art

The use of continuous wave (Doppler shift) radar to measure heart rate of a patient is known. It works on the principle that a beating heart moves and of course a continuous wave radar can detect the presence of motion and its speed. Unfortunately, lung motion caused by breathing and patient movement is also detected by the radar. Further, the periodicity of the heart beat and breathing motions are similar which precludes separating signal components by a frequency filter.

One prior art structure for separating the two signals is as illustrated in U.S. patent application Ser. No. 527,768 filed Aug. 30, 1983 by M. Nowogrodzski and the instant applicant, now U.S. Pat. No. 4,513,748. That structure utilizes two radar frequencies and compares signals corresponding to the return signal at the two frequencies for producing a signal corrresponding to heart rate. Such a circuit, while effective, is relatively costly.

SUMMARY OF THE INVENTION

The present invention is directed to a signal component separating circuit of the type which accepts a signal having a pulsing component coexisting with a reciprocating component where it is desired to utilize the pulsing component. The circuit comprises first and second channels, each receptive of the signal, and coupled to respective inputs of a comparator. Each channel includes a peak detection and holding circuit (PDH) receptive of the input signal and coupled at its output to the comparator, each PDH including a charging and discharging circuit, the second channel PDH having a faster charging and discharging time than the first channel PDH, the second channel PDH attenuating the input signal more than the first channel PDH. The comparator is receptive of the two peak detected and held signals for producing a signal having a component corresponding to the time when the pulsing component of the input signal is present.

DETAILED DESCRIPTION OF A PREFERRED EMBODIMENT

Figure 1:
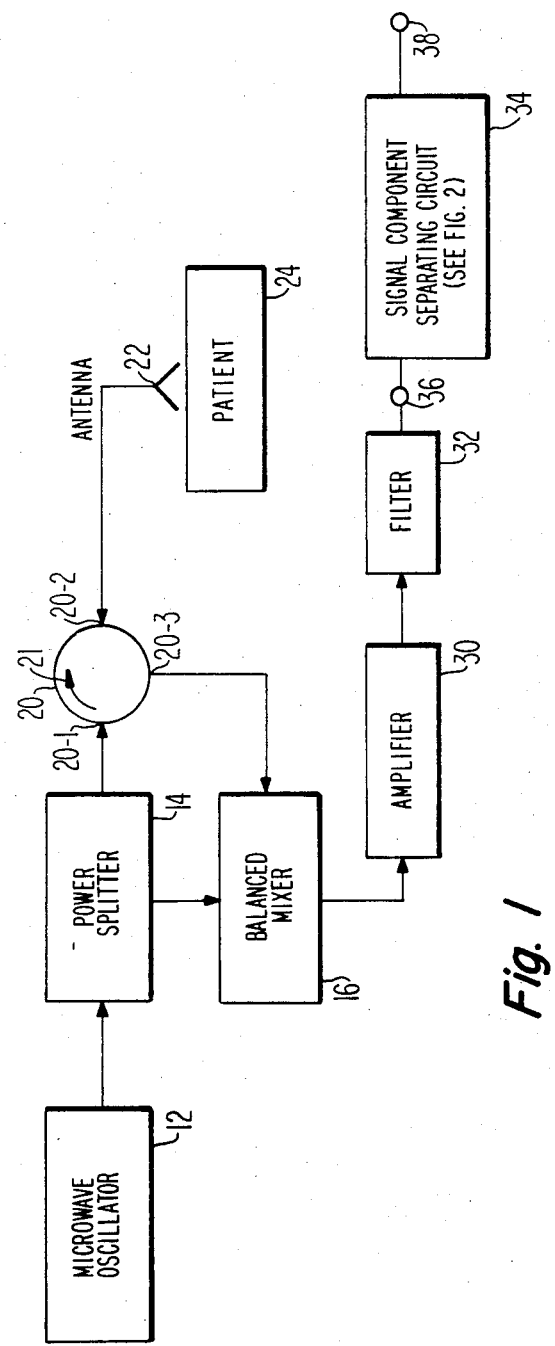
FIG. 1 is an overall system diagram in block schematic form of a continuous wave radar system employing the signal component separating circuit of the instant invention.

FIG. 1, to which attention is now directed, illustrates a microwave radar system capable of detecting a patient's heart rate. In FIG. 1 microwave oscillator 12 produces a continuous wave microwave signal at, for example, 2450 megahertz. The signal produced by microwave oscillator 12 is split into two paths by power splitter 14. One output of power splitter 14 is connected to balanced mixer 16 and the other output is connected to a first port of three-port circulator 20. A second port of circulator 20 is connected to a transmitting/receiving antenna 22.

Antenna 22 which, for example may be a rectangular microstrip patch radiator, is arranged to transmit microwave signals to a patient 24 particularly to the region of the patient which includes the heart and to receive reflected signals back from patient 24.

The signal reflected back to antenn 22 from patient 24 is returned to circulator 20 and emitted at the third port 20-3 thereof. Third port 20-3 is connected to a second input of balanced mixer 16.

A balanced mixer is an arrangement of signal splitting and matching elements and a pair of mixer diodes which tend to cancel oscillator 12 variations while separating out the signal difference components. The output of balanced mixer 16 is coupled to a suitable low level dc-audio frequency amplifier 30. The output of amplifier 30 is connected to a filter 32.

Filter 32 is a bandpass filter which filters out low frequencies below the lowest possibly produced by heart beat in any patient such as signal components due to very slow relative motions between the patient and the instrument or dc level drifts in mixer 16 or battery power source (not shown) used to power the heart rate monitor of FIG. 1. Filter 32 also filters out signal components at frequencies above those associated with the heart beat of a patient such as those due to pick up of radio interference from other sources such as fluorescent lighting.

The output of filter 32 is connected to a signal component separating circuit 34 at its input terminal 36. In a manner to be described hereinafter comparator circuit 34 produces at its output terminal 38 a signal corresponding solely to the rate of heart beat of patient 24. As will also be described hereinafter other signal components relating to breathing of patient 24 and slow patient motion appearing at terminal 36 will be removed by circuit 34. If the patient should have sharp jerky motions, however, these may well pass through circuit 34 to appear at terminal 38.

All components illustrated in FIG. 1 except for circuit 34 are of conventional design. Before describing the construction and operation of circuit 34 the operation of the circuit of FIG. 1 will be given. Microwave oscillator 12 produces a continuous wave microwave signal which passes through power splitter 14, through circulator 20, from port 20-1 to port 20-2 thereof (Arrow 21 indicates direction of signal movement through circulator 20.) and thence to antenna 22 where it is radiated to illuminate patient 24.

Digressing for a moment, if patient 24 were simply a moving vehicle operating at a uniform or nearly uniform speed, the signal emitted by antenna 22 would be reflected back to antenna 22 with a slight phase difference relating to the speed with which the vehicle were moving toward or away from antenna 22. This is the well known doppler shift principle used in police radars.

The motion of a patient 24 is, however, substantially more complex than that of a moving vehicle and therefore the signal returned to antenna 22 reflects this complexity. Thus the signal reflected back to antenna 22 is a function of the movement of the heart within patient 24, the movement of the chest of patient 24 due to breathing and of other movement of patient 24 such as, for example, caused by the patient rolling from side to side or other body movements. Signal reflected back to antenna 22 passes to port 20-2 of circulator 20 and out of port 20-3 to be applied to balanced mixer 16.

The signal produced by balanced mixer 16 again is a function of the type of target illuminated by antenna 22. Thus to use the previous example of a uniformly-moving vehicle, mixer 16 would produce a single low frequency signal corresponding to the continuously-changing phase difference caused by a moving vehicle. The frequency of the signal would represent vehicle speed. However, with a patient's heart and chest moving in a reciprocating or pulsating manner, the mixer output signal will follow the motion of the patient and the envelope of the mixer output signal is representative of the character of the motion. Thus, the envelope of the radar mixer output obtained from monitoring the motion produced by normal respiration will generally be sinusoidal or slowly reciprocating in nature with a frequency corresponding to the patient's breathing rate while the envelope of the mixer signal from monitoring the heart will be much more pulse-like because of the nature of the cardiac action and the resulting surges of blood, muscle and chest wall of the patient. The purpose of circuit 34 to which signal is passed from balanced mixer 16 is to separate the signals due to respiration and heart beat and produce at its output a signal corresponding only to the heart beat of the patient.

Figure 2:
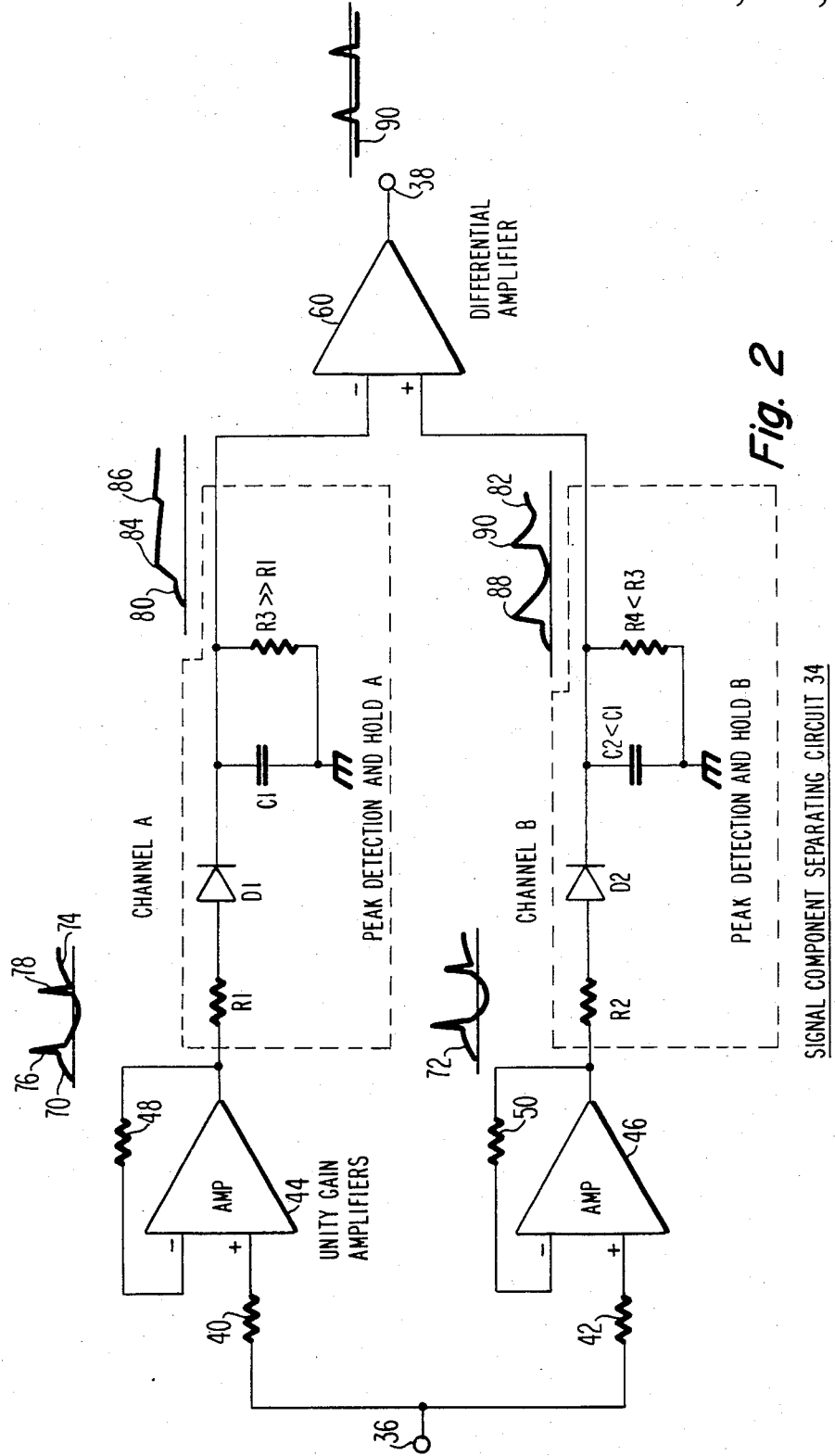
FIG. 2 is a signal component separating circuit in electric block and schematic form in accordance with a preferred embodiment of the present invention.

In FIG. 2 terminals 36 and 38, respectively, correspond to terminals bearing the same respective callouts in FIG. 1. All of the circuitry illustrated in FIG. 2 is that within block 34 of FIG. 1. Terminal 36, FIG. 2, is connected to current limiting resistors 40 and 42 which are connected to the positive (+) inputs of two unity gain amplifiers 44 and 46, respectively. The purpose of unity gain amplifiers 44 and 46 is to provide two identical signals which are isolated from each other to eliminate interaction caused by subsequent signal processing as well as to isolate sensitive analog amplifier circuits such as 30 in FIG. 1 from the pulsating digital processor circuitry (not illustrated) which would be connected to terminal 38.

The outputs of the two amplifiers 44 and 46 are fed back through feedback resistors 48 and 50, respectively, to the negative (−) input of the amplifiers. The output of amplifier 44 is connected in series with resistor R1 and diode D1 to the negative (−) input of a differential amplifier 60. Similarly, the output from amplifier 46 is series connected with resistor R2 and diode D2 to the positive (+) input of differential amplifier 60. A capacitor C1 and resistor R3 are connected in parallel between the cathode of D1 and system ground. Components R1, D1, C1 and R3 form a peak detection and hold circuit A. Similarly, capacitor C2 and resistor R4 are connected in parallel between the cathode of D2 and system ground. Components R2, D2, C2 and R4 form a peak detection and hold circuit B.

For reasons to be discussed hereinafter there is a particular required relationship among the values of the various resistors and capacitors within peak detection and hold circuits A and B. Thus, R1 is set equal to R2, R4 is less than R3, R3 and R4 are much larger than R1 and R2, and C1 is larger than C2. Exemplary values of a working model follow:

R1=68 kilohms R2=68 kilohms
R3=2.2 megohms R4=1.8 megohms
C1=1.5 microfarads C2=0.47 microfarads The signal appearing at terminal 36 and thus the signals appearing at the output of unity gain amplifiers 44 and 46 are as illustrated in waveforms 70 and 72 which are identical and are illustrated in terms of amplitude on the vertical axis and time on the horizontal axis. It will be realized that what is illustrated is an envelope of a high frequency alternating signal emanating from the output of mixer 16 FIG. 1. The envelope signal is in appearance a sinusoidal signal with pulse portions such as 76 and 78 in waveform 70 extending from the sinusoidal portion. Sinusoidal shape portion 74 corresponds to chest and lung movement caused by breathing of the patient while the pulse portions 76 and 78 correspond to heart motions of the patient related to heart rate. It will be noted that the frequencies of the two signal components are approximately equal to one another.

Waveform 80 appearing at the cathode of diode D1 or the negative (−) input of differential amplifier 60 is the result of action on waveform 70 by components R1, D1, C1 and R3. Waveform 80, like waveforms 70 and 72, is illustrated with amplitude on the vertical axis and time on the horizontal axis and is the envelope of a high frequency signal. Likewise, waveform 82 appearing on the cathode of diode D2 or the positive (+) input of difference amplifier 60 also is illustrated with amplitude on the vertical axis and time on the horizontal axis.

The difference between the appearance of waveforms 80 and 82 is due to the difference in component values of C1 relative to C2 and R3 relative to R4. Because C2 is substantially less than C1, waveform 82 tracks waveform 72 much better than waveform 80 tracks waveform 70. Said another way becuase C1 is substantially larger than C2, peak detection and hold circuit A tends to dampen the signals which it affects much more than does peak detection and hold circuit B, thus tending to reduce the effects of spikes 76 and 78. As such portions 84 and 86 of signal 80 corresponding to spikes 76 and 78 are much less pronounced than are portions 88 and 90 respectively of waveform 82 corresponding to spikes 76 and 78. Because R4 is less than R3 or said another way R3 is greater than R4, the signal in channel A is attenuated less than the signal in channel B.

Because of the presence of diodes D1 and D2, the voltages stored on capacitors C1 and C2, respectively, are not affected by subsequent lower input voltages at the anodes of the diodes causing diodes D1 and D2, respectively, to be reverse biased. Thus, the diodes provide a holding effect raising the threshold level through which the spikes must penetrate as the input signal becomes larger providing a self-adaptive triggering level.

The result is that during most times the A channel signal is greater in amplitude than the B channel signal. Only when a spike occurs such as 76 or 78 does the B channel produce a greater in amplitude signal than the A channel. Therefore, most of the time the signal appearing at the minus (−) input of differential amplifier 60 is larger in amplitude than the signal appearing at the positive (+) input and the amplifier is in its low output state. In other words, amplifier 60 produces a relatively low amplitude signal as illustrated in waveform 90 appearing at terminal 38.

Only when waveform 82 is of greater amplitude than waveform 80 is differential amplifier 60 in its high output state and that occurs only when pulses occur corresponding to the patient's heart beat. The resultant pulses in waveform 90 representing only heart beat may be utilized to determine first the presence of heart beat and second the heart beat rate. Heart beat rate can be determined in either of two conventional fashions—one to measure the number of pulses and therefore heart beats in a unit time, or second to measure the time between heart beats.

It will be understood that the circuit of FIG. 2 although described in terms of a circuit distinguishing heart beat from breathing can be utilized to separate a signal having two distinguishable characteristics, each of which occurs with about the same frequency. Thus, for example, the circuit of FIG. 2 could be used for extracting pulse code modulation superimposed on power line for localized signaling and control.

What is claimed is:

1. A signal component separating circuit receptive of a time varying signal having, in amplitude, a pulsing component coexisting with a reciprocating component where it is desired to utilize the pulsing component, comprising in combination:
   a comparator; and
   first and second channels, each receptive of said signal and coupled to respective inputs of said comparator, each of said channels comprising a unity gain amplifier having an input connected to receive said signal and an output and further comprising a peak detection and holding circuit (PDH), the input of which is connected to said output of said unity gain amplifier, each PDH comprising a charging and discharging circuit, wherein the second channel charging and discharging circuit has a faster charging and discharging time than the first channel charging and discharging circuit and wherein the second channel PDH attenuates the input signal more than the first channel PDH such that the first channel signal at said comparator is greater in magnitude than said second channel signal at said comparator except when pulses of said pulsing component are present whereby said comparator is responsive to the first and second channel signals for producing an output signal corresponding to the presence of said pulses.

2. The combination as set forth in claim 1 wherein said first channel PDH comprises a first resistor in series with a diode coupled between said circuit input and said first channel input of said comparator and further includes the parallel combination of a capacitor and second resistor connected between said first channel input of said comparator and system ground and wherein said second channel PDH comprises a third resistor and second diode connected in series between said circuit input and second channel input of said comparator and further including the parallel combination of a second capacitor and fourth resistor connected between said second channel comparator input and system ground.

3. The combination as set forth in claim 2 wherein said fourth resistor is of lower value than said third resistor, wherein said second capacitor is lower in capacitance value than that of said first capacitor and wherein said second and fourth resistors are larger in value than said first and third resistors.

4. The combination as set forth in claim 1 wherein said first channel PDH comprises a first resistor in series with a diode coupled between said unity gain amplifier and said first channel input of said comparator and further includes the parallel combination of a capacitor and second resistor connected between said first channel input of said comparator and system ground and wherein said second channel PDH comprises a third resistor and second diode connected in series between said unity gain amplifier and second channel input of said comparator and further including the parallel combination of a second capacitor and fourth resistor connected between said second channel comparator input and system ground.

5. The combination as set forth in claim 4 wherein said fourth resistor is of lower value than said third resistor, wherein said second capacitor is lower in capacitance value than that of said first capacitor and wherein said second and fourth resistors are larger in value than said first and third resistors.

6. A heart rate monitor comprising a continuous wave microwave transceiver having a transmitting/receiving antenna capable of being directed toward the heart of a patient and, when so directed, for producing a signal having a periodically pulsing component, the period corresponding to the period of successive heart beats and having a reciprocating component corresponding to breathing of said patient, said heart rate monitor further comprising in combination:
   a comparator; and
   first and second channels coupled to receive said pulsing and reciprocating signal,
   said first and second channels being coupled to respective inputs of said comparator, each channel comprising a peak detection and holding circuit (PDH) receptive of said pulsing and reciprocating signal and coupled at its output to the comparator, each PDH comprising a charging and discharging circuit, the second channel charging and discharging circuit having a faster charging and discharging time than the first channel charging and discharging circuit, the second channel PDH attenuating the input signal more than the first channel PDH, said comparator being receptive of the two peak detected and held signals for producing a signal having a component corresponding to the time when the pulsing component of the input signal representing heart beat is present.

7. The combination as set forth in claim 6 wherein each of said channels further includes a unity gain amplifier preceding said PDH.

8. The combination as set forth in claim 7 wherein said first channel PDH comprises a first resistor in series with a diode coupled between said unity gain amplifier and said first channel input of said comparator and further includes the parallel combination of a capacitor and second resistor connected between said first channel input of said comparator and system ground and wherein said second channel PDH comprises a third resistor and second diode connected in series between said unity gain amplifier and second channel input of said comparator and further including the parallel combination of a second capacitor and fourth resistor connected between said second channel input of said comparator and system ground.

9. The combination as set forth in claim 8 wherein said fourth resistor is of lower value than said third resistor, wherein said second capacitor is lower in capacitance value than that of said first capacitor and wherein said second and fourth resistors are larger in value than said first and third resistors.

10. The combination as set forth in claim 6 wherein said first channel comprises a first resistor in series with a diode coupled between said transceiver and said first channel input of said comparator and further includes the parallel combination of a capacitor and second resistor connected between said first channel input of said comparator and system ground and wherein said second channel PDH comprises a third resistor and second diode connected in series between said transceiver and second channel input of said comparator and further including the parallel combination of a second capacitor and fourth resistor connected between said second channel input of said comparator and system ground.

11. The combination as set forth in claim 10 wherein said fourth resistor is of lower value than said third resistor, wherein said second capacitor is lower in capacitance value than that of said first capacitor and wherein said second and fourth resistors are larger in value than said first and third resistors.

* * * * *